United States Patent [19]
Tharpe

[11] Patent Number: 5,870,778
[45] Date of Patent: Feb. 16, 1999

[54] DISPOSABLE UNDERGARMENT WAISTBAND AND METHOD OF FORMING SAME

[76] Inventor: John M. Tharpe, P.O. Box 3970, Albany, Ga. 31706

[21] Appl. No.: 958,144

[22] Filed: Oct. 28, 1997

Related U.S. Application Data

[63] Continuation of Ser. No. 699,110, Aug. 16, 1996, Pat. No. 5,706,524.

[51] Int. Cl.$^6$ ............................. A41D 27/00; A41D 27/24
[52] U.S. Cl. ............................. 2/400; 2/69; 2/76; 2/311; 2/401; 604/385.2; 604/392; 604/393
[58] Field of Search ................................... 2/69, 69.5, 76, 2/60, 78.1, 78.3, 103, 79, 170, 211, 220, 221, 400, 401, 402, 235, 236, 237, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 243.1, 275; 604/385.1, 385.2, 386, 387, 389, 390, 391, 392, 393, 394, 395, 396, 308; 156/177, 179, 183, 229, 291, 301, 161; 428/109, 112, 152, 201, 286; 602/41, 62, 75, 900

[56] References Cited

U.S. PATENT DOCUMENTS

| | | |
|---|---|---|
| 945,635 | 1/1910 | Strauss et al. . |
| 1,183,037 | 5/1916 | Scheuer . |
| 3,762,980 | 10/1973 | Maggio . |
| 3,842,832 | 10/1974 | Wideman et al. . |
| 4,315,508 | 2/1982 | Bolick . |
| 4,446,189 | 5/1984 | Romanek . |
| 4,492,608 | 1/1985 | Hirsch et al. . |
| 4,617,022 | 10/1986 | Pigneul et al. . |
| 4,692,368 | 9/1987 | Taylor et al. . |
| 4,822,435 | 4/1989 | Igaue et al. . |
| 4,883,549 | 11/1989 | Frost et al. . |
| 4,900,384 | 2/1990 | Sanders et al. . |
| 4,904,249 | 2/1990 | Miller . |
| 4,904,332 | 2/1990 | McKeown . |
| 4,932,950 | 6/1990 | Johnson . |
| 4,977,011 | 12/1990 | Smith . |
| 5,030,303 | 7/1991 | Cucuzza . |
| 5,135,522 | 8/1992 | Fahrenkrug et al. . |
| 5,187,817 | 2/1993 | Zolner . |
| 5,190,606 | 3/1993 | Merkatoris et al. . |
| 5,193,225 | 3/1993 | Karami et al. ............................. 2/312 |
| 5,209,801 | 5/1993 | Smith . |
| 5,304,162 | 4/1994 | Kuen . |
| 5,374,262 | 12/1994 | Keuhn, Jr. et al. . |
| 5,386,595 | 2/1995 | Kuen et al. . |
| 5,423,789 | 6/1995 | Kuen . |
| 5,445,628 | 8/1995 | Gipson et al. . |

*Primary Examiner*—Jeanette Chapman
*Attorney, Agent, or Firm*—Allen, Dyer, Doppelt, Milbrath & Gilchrist, P.A.

[57] ABSTRACT

A disposable undergarment waistband and method of forming a waistband are provided which preferably include providing a first elongate layer of non-woven material having a first predetermined width and upper and lower surfaces. A plurality of elongate elastic strips are positioned to overlie a first portion of the upper surface of the first non-woven layer. A second elongate layer of non-woven material preferably is also provided having a second predetermined width and upper and lower surfaces. The lower surface of the second elongate layer is positioned to overlie the plurality of elastic strips and the upper surface of the first portion of said first non-woven elongate layer. The second predetermined width of the second non-woven layer preferably is narrower than the first predetermined width of the first non-woven layer. The upper surface of at least a second portion of the first elongate layer preferably is folded to overlie and to be secured to the upper surface of the second elongate layer. A plurality of gathers also are formed in the first and second non-woven layers.

18 Claims, 4 Drawing Sheets

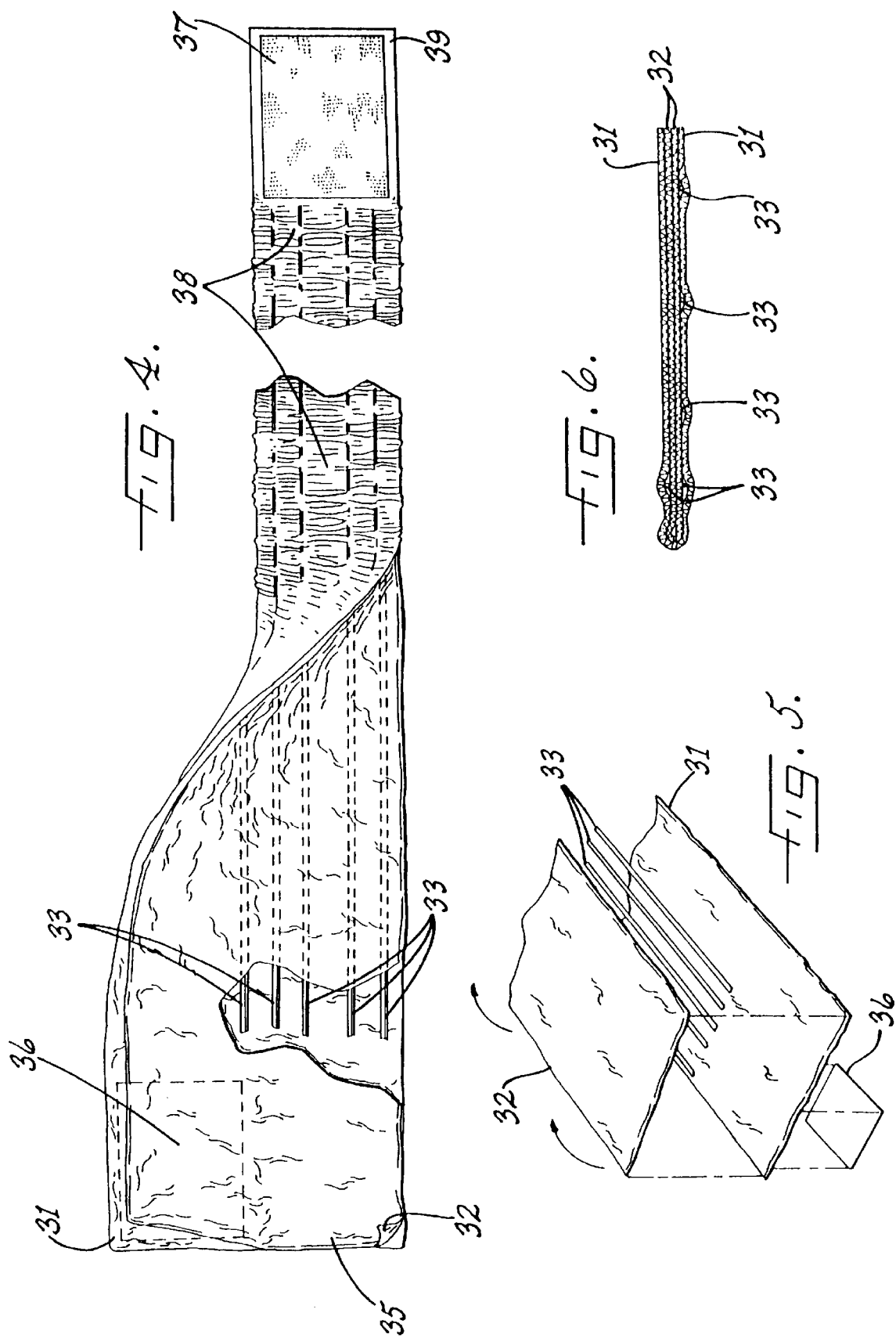

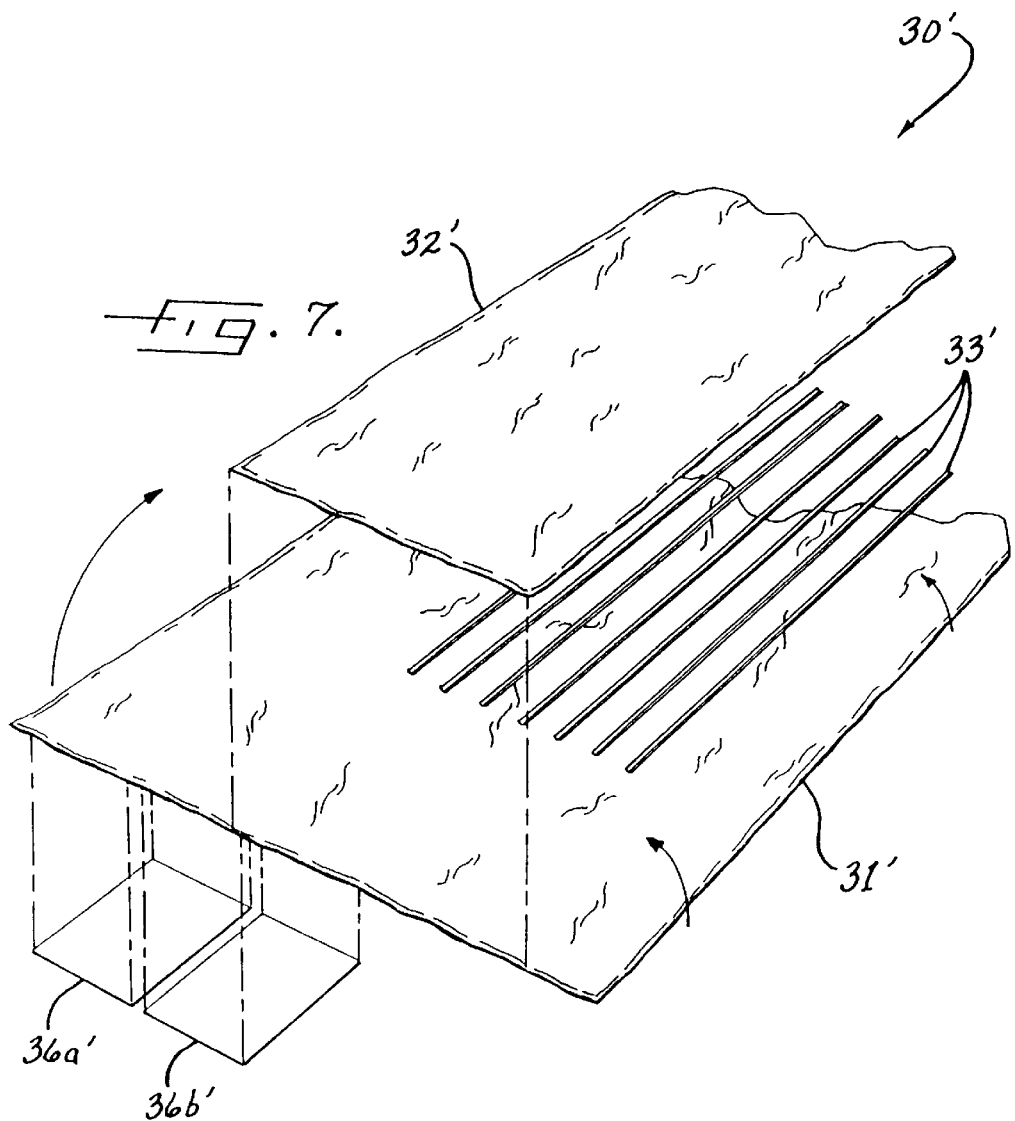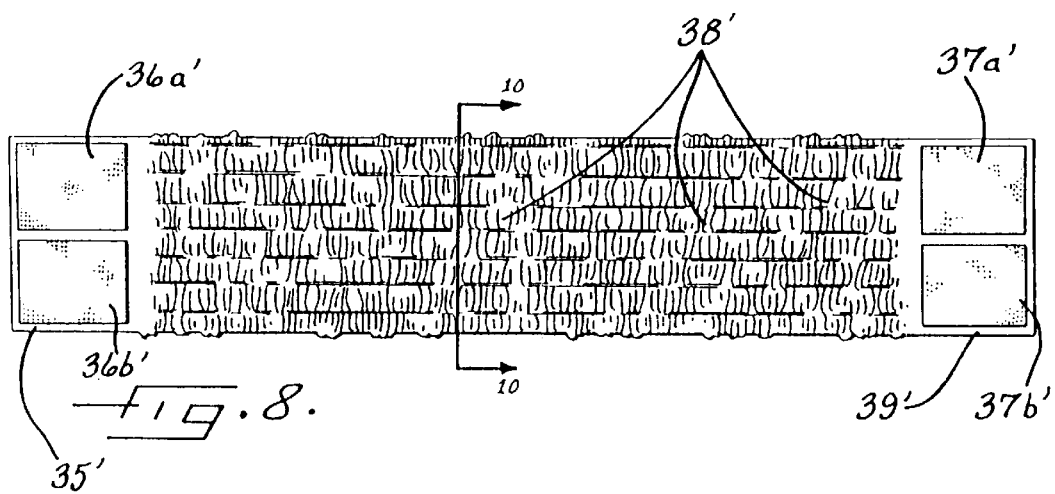

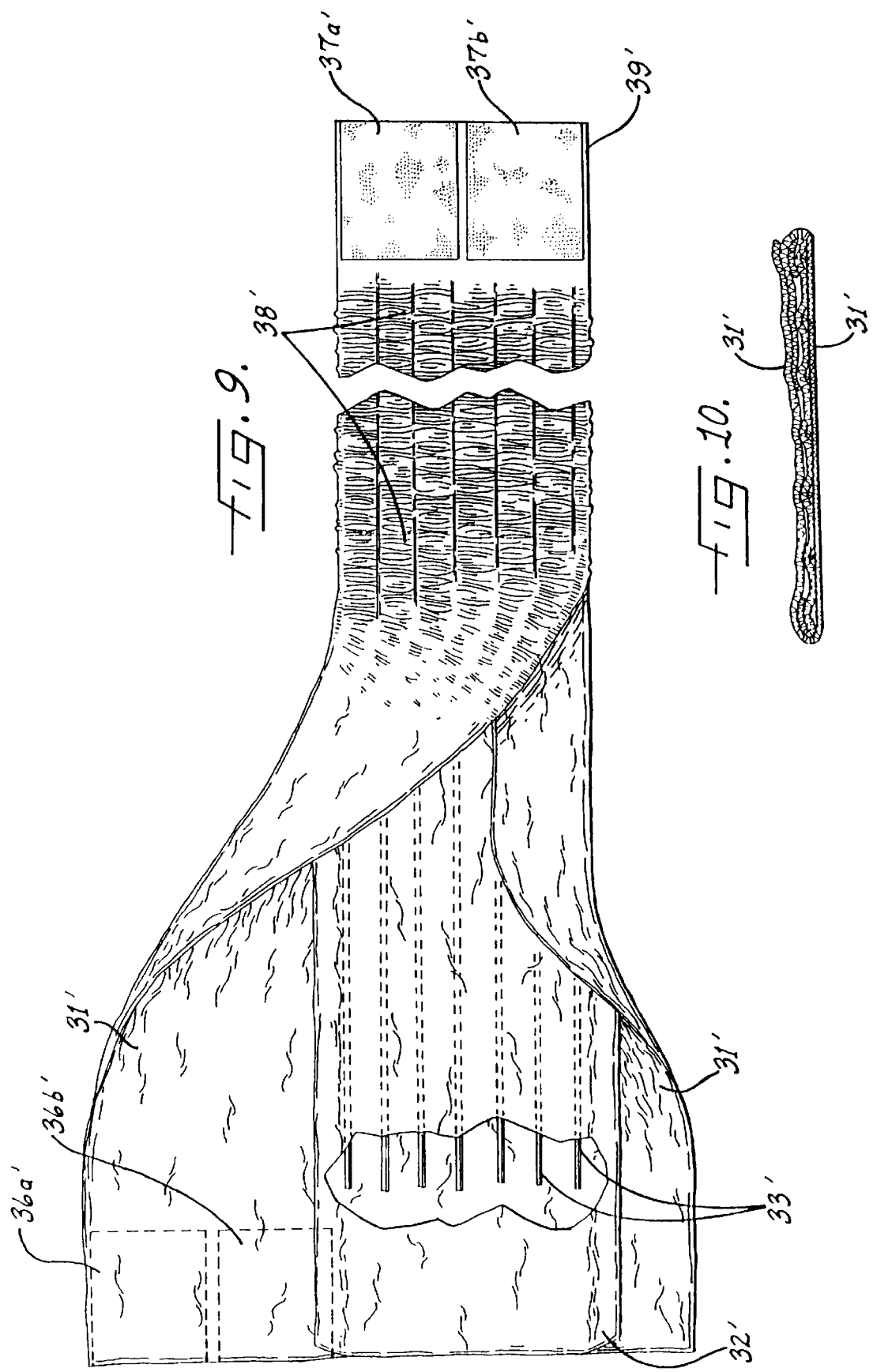

DISPOSABLE UNDERGARMENT WAISTBAND AND METHOD OF FORMING SAME

This application is a continuation of Ser. No. 08/699,110 filed on Aug. 16, 1996, now U.S. Pat. No. 5,706,524.

FIELD OF THE INVENTION

This application is related to the manufacture of disposable products and, more particular, to undergarment waistbands and methods of forming waistbands.

BACKGROUND OF THE INVENTION

Over the years, consumers have shifted demand from cloth diapers to disposable diapers for infants and toddlers. This demand has increased and developed the disposable diaper industry into a major industry. As this industry developed, consumers preferred and often demanded improvements in disposable products which included better core absorbency, products which are easier to fasten, detach, and reattach side peripheries of the waistbands, various sizes of products for various weights and sizes of infants and toddler, and better control of leakage from the legs and waistbands when the diaper is positioned on an infant or toddler.

This development of the disposable diaper industry, however, has increased demand for faster and more efficient disposable undergarment production. This demand is further complicated by the development of disposable infant, toddler, and adult briefs, which have a different product configuration and have different product performance requirements than disposable diapers. Also because of the relative success of the disposable diapers and the high volume of disposable diaper products produced in manufacturing, the market for these brief products has generally been a much smaller subset of the infant and toddler disposable diaper market. The demand for briefs in general is substantially less than the disposable diapers. Accordingly, these specially configured briefs are not normally produced on the same production line as the disposable diaper production line. Because the market demand for these briefs is less, product manufacturers are less inclined to invest in additional machinery for producing these products. The product manufacturer, however, is also pushed by retailers and consumers to provide a full-line of disposable products for infants and toddlers.

Additionally, as the nursing home care and elderly care industry has grown over the years, the elderly often have needed more and more assistance from nursing home or elderly care personnel, including urination and bowel movement assistance. Urination and bowel movement problems have also arisen among various aged adults such as loss of bladder control through childbirth or other medical reasons.

Further, waistbands have been developed over the years which are secured to various undergarments along a stitch line formed on upper front, rear, and side peripheries of an undergarment fabric panel. Waistband straps and belts have also been developed which have one end secured to or otherwise fastened to an upper rear periphery of an undergarment fabric panel, extend outwardly therefrom, and have the other end secured or otherwise fastened (e.g., buttoned) to an upper front periphery of the same undergarment fabric panel.

Nevertheless, these conventional waistbands are often expensive, formed of a heavy fabric or single elastic sheet, and can be used multiple times until damage, staining, or the like. Example's of these conventional waistbands are illustrated in U.S. Pat. No. 4,315,508 titled "Self-Centering Multiple Use Garment Suspension System", by Bolick and U.S. Pat. No. 4,904,249 titled "Absorbent Undergarment With Fluid Transfer Layer And Elasticized Crotoa Design" by Miller et al. This expense and lack of disposability become particularly problematic when manufacturing disposable undergarments in high volume and at a high rate of speed. In other words, the waistband of conventional undergarments are either not applicable or make up too much of the cost of manufacturing an undergarment so that the undergarment is cost prohibitive or much less competitive to manufacture.

Additionally, waistbands or belts for attaching and detaching to an undergarment panel have been developed for hygienic articles. Examples of these waistbands or belts are illustrated in U.S. Pat. No. 4,617,022 titled "Disposable Hygienic Article With Removable Belt" by Pigneul et al., U.S. Pat. No. 5,304,162 titled "Carment And Pleated, Adjustable Strap Member Therefor" by Kuen, and U.S. Pat. No. 5,374,262 titled "Adjustable Garment Attachment System" by Keuhn, Jr. et al. These waistbands and belts, however, often have a complex construction, are expensive and difficult to manufacture in high volume, and often lack the necessary elasticity and comfort for wearers of the undergarment and waistband.

Further, disposable elastic structures have been developed which include a complex arrangement of a single elastic strip or a plurality of elastic strips and a layer of adhesive tape positioned between layers of non-woven material. Examples of these structures are illustrated in U.S. Pat. No. 5,209,801 titled "Method Of Forming A Disposable Elastic Structure" by Smith and U.S. Pat. No. 4,977,011 titled "Disposable Elastic Structure" by Smith. These structures, however, are likewise still relatively expensive and difficult to manufacture in high volume, and often lack the necessary comfort for wearers of a disposable undergarment and waistband. The structures generally are also constructed to be integrally formed with the undergarment panel and not detachably connected to the panel.

OBJECTS AND SUMMARY OF THE INVENTION

With the foregoing in mind, it is an object of the present invention to provide a disposable undergarment waistband and a method for forming disposable undergarment waistbands more efficiently.

It is also an object of the present invention to provide a disposable undergarment waistband and a method of producing the waistband at a high production speed that comfortably contacts the skin of wearer.

It is another object of the present invention to provide a disposable undergarment waistband that has good stretching and recovery characteristics and that easily attaches and detaches to a disposable undergarment panel.

It is also another object of the present invention to provide a less expensive disposable undergarment waistband that can be readily produced in high volume.

These objects and other advantageous of the present invention are provided by a disposable undergarment waistband which preferably includes in a first embodiment thereof a first elongate layer of non-woven material having a first predetermined width and upper and lower surfaces. A plurality of elongate elastic strips are positioned to overlie a first portion of the upper surface of the first non-woven layer. A second elongate layer of non-woven material is provided which preferably has a second predetermined width and upper and lower surfaces. The lower surface of the second elongate layer is positioned to overlie the plurality of elastic strips and the upper surface of the first portion of the first non-woven elongate layer. The second predetermined width of the second non-woven layer is preferably narrower than the first predetermined width of the first non-woven layer.

The upper surface of at least a second portion of the first elongate layer preferably is folded to overlie and secure to the upper surface of the second elongate layer, and a plurality of gathers preferably are formed in the first and second non-woven layers. According to a first embodiment of the present invention, the second layer preferably also includes first and second portions. The lower surface of the first portion of the second layer overlies the plurality of elongate elastic strips. The lower surface of the second portion of the second layer overlies the second portion of the first layer. The second portion of the first layer is folded so that the upper surface of the second portion of the second layer overlies the upper surface of the first portion of the second layer and the lower surface of the second portion of the second layer underlies the upper surface of the folded second portion of the first layer. These folded first and second layers provide a smooth and comfortable surface for what becomes the upper end of the waistband when positioned on a wearer. This fold also inhibits skin irritation and upper portions of the waistband from digging into the skin of a wearer.

In a second embodiment of a disposable undergarment waistband according to the present invention, the first predetermined width of the first layer preferably is substantially greater (e.g., two times greater) than the second predetermined width of the second layer. The at least a second portion of the first layer preferably includes second and third portions. The upper surface of the third portion is folded to overlie and be secured to at least portions of the upper surface of the second layer. The upper surface of the second portion is folded to overlie and be secured to portions of the upper surface of the second elongate layer and portions of the lower surface of the folded third portion of the first layer. This embodiment of a waistband provides two folded portions of the first layer and also provides smooth and comfortable surfaces for what becomes the upper and lower ends of the waistband when positioned on a wearer and attached to an undergarment panel. These folds also inhibit skin irritation and upper portions of the waistband from digging into the skin of a wearer.

Additionally, the first and second embodiments of a disposable undergarment waistband preferably also include non-elasticized end portions of the first and second layers and either a hook or a loop type fastener secured to each of the end portions for fastening to a mating hook or loop type fastener secured to an upper peripheral end portion of a disposable undergarment panel. These hook or loop type fasteners provide an inexpensive fastener which can be readily secured to a disposable waistband product, and yet this type of fastener provides a simple fastening mechanism which are likely to be already familiar to wearers of the undergarment.

The present invention also includes a method of forming a disposable undergarment waistband. The method preferably includes providing a first layer of elongate fabric material having a first predetermined width and upper and lower surfaces and securing a plurality of stretched elongate elastic strips to a first portion of the upper surface of the first fabric layer. A second layer of elongate fabric material having a second predetermined width and upper and lower surfaces is positioned so that the lower surface of the second elongate layer overlie the plurality of elastic strips and the upper surface of the first portion of the first elongate layer. The second predetermined width of the second non-woven layer is preferably narrower than the first predetermined width of the first layer.

According to a first embodiment of the method, at least a second portion of the first layer is folded so that the upper surface of the second portion of the first layer overlies the second layer. The first fabric layer is secured to the second fabric layer such as by an ultrasonic seal. The second layer also preferably includes first and second portions. The lower surface of the first portion of the second layer overlies the plurality of elongate elastic strips. The lower surface of the second portion of the second layer overlies the second portion of the first layer. The step of folding the second portion of the first layer preferably includes folding the second portion of the first and second layers so that the upper surface of the second portion of the second layer overlies the upper surface of the first portion of the second layer and the lower surface of the second portion of the second layer underlies the upper surface of the folded second portion of the first layer.

The method of forming a disposable undergarment waistband preferably further includes relaxing the plurality of stretched elastic strips so as to form a plurality of gathers in the first and second non-woven layers. A uniform adhesive pattern is formed on the upper surface of the first layer to secure the plurality of elongate elastic strips thereto. Also, at least a first portion of the second layer can be folded so that the upper surface of a first portion of the second layer overlies the upper surface of a second portion of the second layer. At least one fastener is also preferably secured to each respective end portion of the waistband to thereby secure a disposable undergarment panel thereto.

A disposable undergarment waistband and method of the present invention advantageously provide a flexible and cost efficient disposable undergarment waistband which can readily attach to numerous types and sizes of disposable undergarments including those produced in a high speed production process. The first and second layers, for example, can inexpensively be formed by dividing an existing sheet of fabric material into a plurality of layer strips for forming the waistbands. The formed waistbands can then be cut either before or after the fasteners are secured to the waistband. The waistband and method enhance current manufacturers ability to produce various configurations of undergarments in a cost efficient process, especially where the particular configurations are demanded or needed by the market but the volume, for example, is significantly less than other product configurations.

BRIEF DESCRIPTION OF THE DRAWINGS

Some of the objects, features, advantages, and uses of the present invention having been stated, others will become more apparent by referring to the following detailed description and drawings in which:

FIG. 4 is a fragmentary top plan view of a disposable undergarment waistband having portions thereof broken away for clarity according to a first embodiment of the present invention;

FIG. 5 is a fragmentary exploded view of an end portion of a disposable undergarment waistband according to a first embodiment of the present invention;

FIG. 6 is a vertical sectional view of a disposable waistband product according to a first embodiment of the present invention taken along line 6—6 of FIG. 3;

FIG. 7 is a fragmentary exploded view of an end portion of a disposable undergarment waistband according to a second embodiment of the present invention;

FIG. 8 is a top plan view of a disposable undergarment waistband according to a second embodiment of the present invention;

FIG. 9 is a fragmentary top plan view of a disposable undergarment waistband having portions thereof broken away for clarity according to a second embodiment of the present invention; and FIG. 10 is a vertical sectional view of a disposable waistband product according to a second embodiment of the present invention taken along line 10—10 of FIG. 8.

DETAILED DESCRIPTION

The present invention will now be described more fully hereinafter with reference to the accompanying drawings in which preferred embodiments of the invention are shown. This invention, however, can be embodied in many different forms and should not be construed as limited to the illustrated embodiments set forth herein. Rather, applicants provide these embodiments so that this disclosure will be thorough and complete, and will fully convey the scope of the invention to those skilled in the art. Like numbers refer to like elements throughout.

Figure 1:
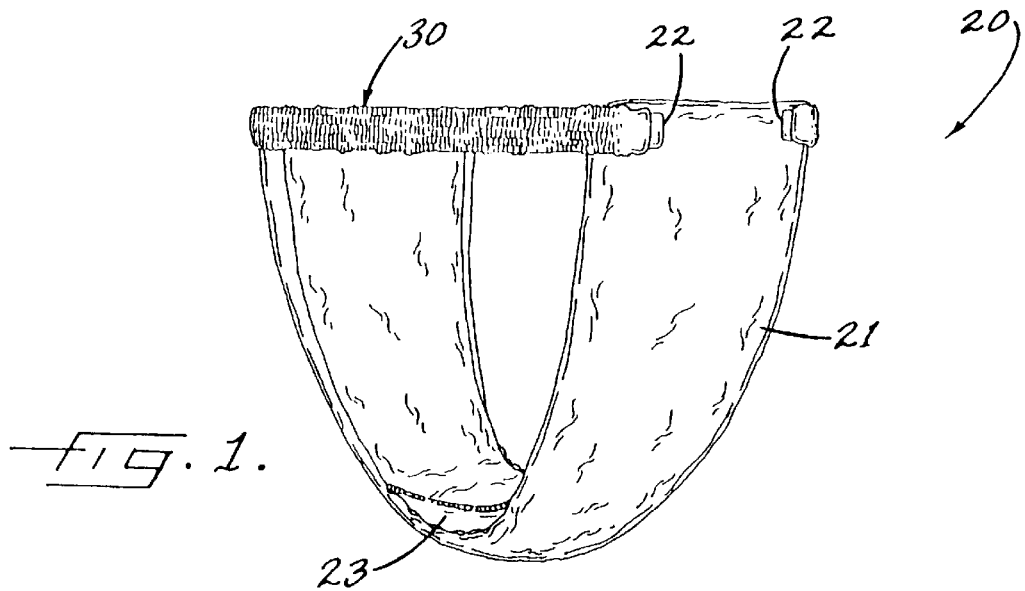
FIG. 1 is a perspective view of a disposable undergarment having a disposable undergarment waistband secured to upper peripheral end portions of a disposable undergarment panel according to the present invention.
Figure 2:
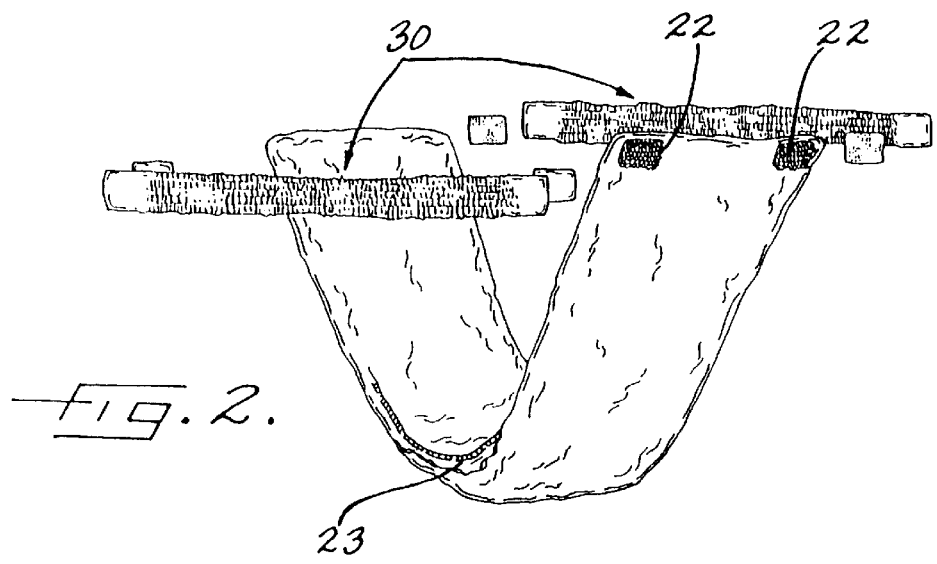
FIG. 2 is an exploded perspective view of a disposable undergarment having a disposable undergarment waistband secured to upper peripheral end portions of a disposable undergarment panel according to the present invention.
Figure 3:
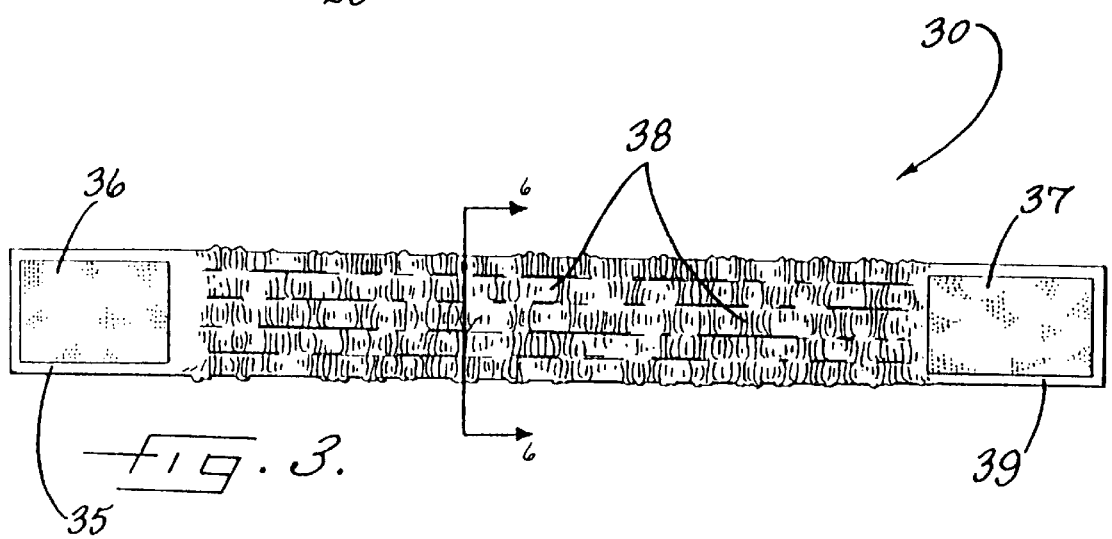
FIG. 3 is a top plan view of a disposable undergarment waistband according to a first embodiment of the present invention.

FIGS. 1–2 illustrate a disposable undergarment 20 having a pair disposable undergarment waistbands 30 detachably connected to upper peripheral portions of an undergarment panel 21 according to the present invention. As best illustrated in FIGS. 3–6, a first embodiment of a disposable undergarment waistband 30 according to the present invention preferably has a first elongate layer 31 of non-woven material having a first predetermined width and upper and lower surfaces. A plurality of elongate elastic strips 33 are positioned to overlie a first portion of the upper surface of the first non-woven layer 31. An adhesive or glue preferably is positioned in a uniform pattern, e.g., by using a rotating motion of an adhesive applicator head, along the upper surface of the first layer 31 for securing the plurality of elongate elastic strips 33 thereto. A second elongate layer 32, including upper and lower surfaces, of non-woven material is positioned so that a lower surface thereof overlies the plurality of elastic strips 33 and the upper surface of the first portion of the first non-woven elongate layer 31. The first and second layers 31, 32 are preferably non-woven fabric material which can either be breathable or non-breathable. The fabric material preferably includes a plastic or polymeric material either formed integrally therewith or attached as a thin layer to the non-woven material to provide securing of the layers 31, 32 as described further herein.

The second elongate layer 32 preferably has a second predetermined width which is narrower than the first predetermined width of the first non-woven layer 31. According to a second embodiment of the present invention, as best illustrated in FIGS. 7–10 and having like elements designated with prime (') notation, the first predetermined width of the first layer 31' is substantially greater (e.g., about two times greater) than the second predetermined width of the second layer 32'.

The upper surface of at least a second portion of the first elongate layer 31 is folded to overlie and secured to the upper surface of the second elongate layer 32 so that the lower surface of the at least a second portion of the first elongate non-woven layer 31 can be comfortably positioned to abuttingly contact the skin of a wearer. As best illustrated in FIGS. 4–5, including the arrows illustrated therein, the second layer 32 preferably also includes first and second portions. The lower surface of the first portion of the second layer 32 overlies the plurality of elongate elastic strips 33. The lower surface of the second portion of the second layer 32 overlies the second portion of the first layer 31. The second portion of the first layer is folded so that the upper surface of the second portion of the second layer 32 overlies the upper surface of the first portion of the second layer 32 and the lower surface of the second portion of the second layer 32 underlies the upper surface of the folded second portion of the first layer 31.

As best illustrated in FIG. 6, at least a first portion of the second layer 32 can also be folded so that the upper surface of a first portion of the second layer 32 overlie the upper surface of a second portion of the second layer 32. The first and second layers 31, 32 also include non-elastic end portions 35, 39 thereof. A plurality of gathers 38 are formed in the first and second non-woven layers 31, 32, and a fastener 36, 37 is secured to each respective end portion 35, 39 of the waistband 30 for securing to a disposable undergarment. More particularly, the plurality of elastic strips 33 are secured to the upper surface of the first portion of the first layer 31 in a stretched position so that when the plurality of elastic strips 33 are relaxed after securing the second layer 32 to the first layer 31 the plurality of gathers 38 are formed in the first and second layers 31, 32 to thereby provide a waistband 30 that comfortably stretches to various lengths of waists of a user thereof.

The fastener 36, 37 preferably is either a hook or a loop type fastener for fastening to a mating hook or loop type fastener 22 secured to an upper peripheral end portion of a disposable undergarment panel 21. In a second embodiment of a disposable waistband product 30', the fastener 36, 37 preferably is a first fastener 36a', 37a', and the waistband further includes a second fastener 36b', 37b' also preferably being either a hook or loop type fastener for fastening to a mating hook or loop type fastener 22 secured to an upper peripheral end portion of a disposable undergarment panel 21. These hook or loop type fasteners 36, 37 provide an inexpensive fastener which can be readily secured to a disposable waistband product 30 by an adhesive material, and yet this type of fastener 36, 37 provides a simple fastening mechanism, e.g., hooks matingly fastening to loops, which are likely to be already familiar to wearers of the undergarment 20.

As best illustrated in FIGS. 7–10, a second embodiment of a disposable undergarment waistband 30' preferably includes the first layer 31' having second and third portions. The upper surface of the third portion of the first layer 31' is folded to overlie and be secured to at least portions of the upper surface of the second layer 32'. The upper surface of the second portion of the first layer 31' is folded to overlie and be secured to portions of the upper surface of the second elongate layer 32' and portions of the lower surface of the folded third portion of the first layer 31'. This embodiment of a waistband 30', for example, provides two folded portions of the first layer 31' and also provides smooth and comfortable surfaces for what becomes the upper and lower ends of the waistband 30' when positioned on a wearer and attached to an undergarment panel 21. These folds also inhibit skin irritation and upper portions of the waistband 30' from digging into the skin of a wearer.

The present invention, as illustrated in FIGS. 1–10, also provides a method of forming a disposable undergarment waistband 30. The method preferably includes providing a first elongate layer 31 of non-woven material having a first predetermined width and upper and lower surfaces and securing a plurality of stretched elongate elastic strips 33 to the upper surface of a first portion of the first non-woven layer 31. A uniform adhesive pattern (e.g., spiral-shaped) preferably is formed on the upper surface of the first layer 31 to secure the plurality of elongate elastic strips 33 thereto. A lower surface of a second elongate layer 32 of non-woven material is positioned to overlie the plurality of elastic strips 33 and the upper surface of the first portion of the first non-woven elongate layer 31. As described previously, the second elongate layer 32 preferably has a second predetermined width narrower which is than the first predetermined width of the first non-woven layer 31.

At least a second portion of the first layer 31 is folded so that the upper surface of the at least a second portion thereof overlies the upper surface of the second elongate layer 32. The second layer 32 also preferably includes first an second portions. The lower surface of the first portion of the second layer overlies the plurality of elongate elastic strips 33. The lower surface of the second portion of the second layer 32 overlies the second portion of the first layer 31. As best illustrated by FIGS. 4 and 5, including the arrows therein, the step of folding the second portion of the first layer 31 preferably includes folding the second portion of the first and second layers 31, 32 so that the upper surface of the second portion of the second layer 32 overlies the upper surface of the first portion of the second layer 32 and the lower surface of the second portion of the second layer 32 underlies the upper surface of the folded second portion of the first layer 31.

The first layer 31 is then secured to the second layer preferably by an ultrasonic seal such as supplied from an ultrasonic welder which heats and melts the plastic material in at least one of the layers 31, 32 and later cools to form the secure seal. The plurality of stretched elastic strips 33 are then relaxed so as to form a plurality of gathers in the first and second non-woven layers 31, 32. A fastener 36, 37 is secured to each respective end portion 35, 39 of the waistband 30 to thereby secure a disposable undergarment panel 21 thereto. Also, according to a first embodiment of a method of the present invention and as best illustrated in FIG. 6, at least a first portion of the second layer 32 also is folded so that the upper surface of a first portion of the second layer 32 overlies the upper surface of a second portion of the second layer 32.

Additionally, according to a second embodiment of a method according to the present invention, the first predetermined width of the first layer 31' is substantially greater (e.g., about two times greater) than the second predetermined width of the second layer 32'. The at least a second portion of the first layer 31' preferably includes second and third portions. The upper surface of the third portion of the first layer 31' is folded to overlie and be secured to at least portions of the upper surface of the second layer 32'. The upper surface of the second portion is folded to overlie and be secured to portions of the upper surface of the second elongate layer 32' and portions of the lower surface of the folded third portion of the first layer 31'.

An example of an apparatus which illustrates methods of forming a disposable undergarment waistband 30 according to the present invention will now be described herein. It will be understood by those skilled in the art, however, that other embodiments of an apparatus can also be used according to a method and waistband product of the present invention. Elastic waistband forming means, e.g., a waistband former, preferably is positioned to form either a continuous or a plurality of disposable undergarment waistbands 30 extending along a path of travel or direction of manufacture. The waistband forming means can include dividing means, e.g., a sheet divider, for dividing a continuous sheet of non-woven material supplied from a non-woven sheet source into the plurality of continuous strips or layers 31, 32 and strip combining means, e.g., a strip combiner, for combining a plurality of strips of elastic material 33 from a waistband elastic supply source with the plurality of continuous strips of non-woven material. The first and second layers, for example, can inexpensively be formed by dividing an existing sheet of non-woven fabric material into a plurality of layer strips for forming the waistbands. The formed waistbands can then be cut either before or after the fasteners are secured to the waistband.

The plurality of continuous layers as described above preferably includes four strips or layers of non-woven material. These four strips, e.g., cut by the divider, form two pairs of continuous waistband strips. Each waistband has an upper and a lower non-woven strip or layer (e.g., first and second layers 31, 32) and one or more, e.g., preferably four, elastic strips 33 positioned therebetween. Two of the four non-woven layer strips 31, 32 preferably have greater widths than the other two non-woven layer strips. The one or more elastic strips 33 preferably are only adhered to a medial portion of the lower non-woven layer strips 31 so that lengthwise periphery portions of the lower non-woven layer strips 31 remain unelasticized. After the upper and lower non-woven layer strips 31, 32 and the plurality of elastic strip(s) 33 are combined, one of the non-elasticized lengthwise periphery portions of each upper non-woven layer strip 32 is folded by a folding guide member so as to now overlie and adhere to at least lengthwise peripheries of the upper non-woven strip. These folds, for example, will provide a smooth closure or sealed surfaces to the waistbands and will eventually downstream become the upper and lower ends of the waistband of the undergarment.

The one or more elastic strips 33 preferably are adhered to and positioned between the upper and lower non-woven layer strips 31, 32 in an extended position so that when released to the retracted or relaxed position, the waistbands 30 have a plurality of gathers 38 formed therein. This, for example, allows the waistbands 30 which eventually become the waistbands 30 of the undergarments 20 to be stretched when positioning the undergarment 20 on a user to thereby provide a snug and comfortable fit to the waist of a user when retracted or relaxed.

Many modifications and other embodiments of the invention will come to the mind of one skilled in the art having the benefit of the teachings presented in the foregoing descriptions and the associated drawings. Accordingly, it is understood that the invention is not to be limited to the illustrated embodiments disclosed, and that the modifications and embodiments are intended to be included within the spirit and scope of the invention as described in the foregoing specification and as defined in the appended claims.

That which is claimed is:

1. A disposable undergarment waistband comprising:

a first elongate layer of material having a first predetermined width and upper and lower surfaces;

a plurality of elongate elastic strips positioned to overlie a first portion of the upper surface of said first layer;

a second elongate layer of material having a second predetermined width and upper and lower surfaces, the lower surface of said second elongate layer being positioned to overlie said plurality of elastic strips and the upper surface of said first portion of said first elongate layer;

the upper surface of at least a second portion of said first elongate layer being folded to overlie and secured to said second elongate layer so that the lower surface of the at least a second portion of the first elongate layer can be comfortably positioned to abuttingly contact the skin of a wearer; and a plurality of gathers formed in said first and second layers.

2. A disposable undergarment waistband as defined in claim 1, comprising a fastener secured to each respective end portion of the waistband for securing to a disposable undergarment.

3. A disposable undergarment waistband as defined in claim 2, wherein said second layer includes first and second portions, the lower surface of said first portion of said second layer overlying said plurality of elongate elastic strips, the lower surface of said second portion of said second layer overlying said second portion of said first layer, and wherein said second portion of said first layer is folded so that the upper surface of said second portion of said second layer overlies the upper surface of said first portion of said second layer and the lower surface of said second portion of said second layer underlies the upper surface of the folded second portion of said first layer.

4. A disposable undergarment waistband as defined in claim 3, wherein the first predetermined width of said first layer is about two times greater than the second predetermined width of said second layer.

5. A disposable undergarment waistband as defined in claim 1, wherein said at least a second portion of said first layer comprises second and third portions, wherein the upper surface of said third portion is folded to overlie and is secured to at least portions of the upper surface of said second layer, and wherein the upper surface of said second portion is folded to overlie and is secured to portions of the upper surface of said second elongate layer and portions of the lower surface of said folded third portion of said first layer.

6. A disposable undergarment waistband as defined in claim 5, further comprising adhesive positioned in a uniform pattern along the upper surface of said first layer for securing the plurality of elongate elastic strips thereto.

7. A disposable undergarment waistband as defined in claim 6, wherein said fastener comprises either a hook or a loop type fastener for fastening to a mating hook or loop type fastener secured to an upper peripheral end portion of a disposable undergarment panel.

8. A disposable undergarment waistband as defined in claim 7, wherein said fastener comprises a first fastener, and wherein the waistband further includes a second fastener also comprising either a hook or loop type fastener for fastening to a mating hook or loop type fastener secured to an upper peripheral end portion of a disposable undergarment panel.

9. A disposable undergarment waistband as defined in claim 8, wherein said first and second layers include non-elastic end portions thereof, and wherein said fastener is secured to said non-elastic end portions of the waistband.

10. A disposable undergarment waistband as defined in claim 9, wherein said plurality of elastic strips are secured to the upper surface of said first portion of said first layer in a stretched position so that when said plurality of elastic strips are relaxed after securing said second layer to said first layer said plurality of gathers are formed in said first and second layers to thereby provide a waistband that stretches to various lengths of waists of a user thereof.

11. A disposable undergarment waistband as defined in claim 10, wherein at least a first portion of said second layer is also folded so that the upper surface of a first portion of the second layer overlie the upper surface of a second portion of said second layer.

12. A method of forming a disposable undergarment waistband comprising:

providing a first layer of elongate fabric material having a first predetermined width and upper and lower surfaces;

securing a plurality of stretched elongate elastic strips to a first portion of the upper surface of the first fabric layer;

positioning a second layer of elongate fabric material having a second predetermined width and upper and lower surfaces so that the lower surface of the second elongate layer is positioned to overlie the plurality of elastic strips and the upper surface of the first portion of the first elongate layer;

folding at least a second portion of the first layer so that the upper surface of the second portion of the first layer overlies said second layer; and securing the first fabric layer to the second fabric layer.

13. A method as defined in claim 12, wherein the second layer also includes first and second portions, the lower surface of the first portion of the second layer overlying the plurality of elongate elastic strips, the lower surface of the second portion of the second layer overlying the second portion of the first layer, and wherein the step of folding the second portion of the first layer includes folding the second portion of the first and second layers so that the upper surface of the second portion of the second layer overlies the upper surface of the first portion of the second layer and the lower surface of the second portion of the second layer underlies the upper surface of the folded second portion of the first layer.

14. A method as defined in claim 13, further comprising relaxing the plurality of stretched elastic strips so as to form a plurality of gathers in the first and second non-woven layers.

15. A method as defined in claim 14, wherein the at least a second portion of the first layer comprises second and third portions, and wherein the method further comprises folding the upper surface of the third portion of the first layer to overlie and be secured to at least portions of the upper surface of the second layer, and wherein the upper surface of the second portion is folded to overlie and be secured to portions of the upper surface of the second elongate layer and portions of the lower surface of the folded third portion of the first layer.

16. A method as defined in claim 15, further comprising forming a uniform adhesive pattern on the upper surface of the first layer to secure the plurality of elongate elastic strips thereto.

17. A method as defined in claim 16, further comprising folding at least a first portion of the second layer so that the upper surface of a first portion of the second layer overlies the upper surface of a second portion of the second layer.

18. A method as defined in claim 12, further comprising securing at least one fastener to each respective end portion of the waistband to thereby secure a disposable undergarment panel thereto.

\* \* \* \* \*